United States Patent [19]
Fields et al.

[11] Patent Number: 5,437,635
[45] Date of Patent: Aug. 1, 1995

[54] TUBE FLOW LIMITER, SAFETY FLOW CLIP, AND TUBE PINCHER MECHANISM

[75] Inventors: Antony Fields, San Francisco, Calif.; Terry Branson, Round Rock, Tex.; David J. Harrison, Carrollton, Tex.; Dana J. Owens, Irving, Tex.; Aaron T. Raines, Dallas, Tex.; Edward G. Rasmussen, Carrollton, Tex.

[73] Assignee: McGaw, Inc., Carrollton, Tex.

[21] Appl. No.: 167,413

[22] Filed: Dec. 14, 1993

Related U.S. Application Data

[63] Continuation-in-part of Ser. No. 880,642, May 6, 1992, abandoned.

[51] Int. Cl.⁶ ............................................ A61M 31/00
[52] U.S. Cl. ....................................... 604/65; 604/153; 604/250; 128/DIG. 12
[58] Field of Search ........................... 604/4-6, 604/34, 65-67, 151, 153, 245, 246, 250; 128/DIG. 12, DIG. 13; 251/7, 9

[56] References Cited

U.S. PATENT DOCUMENTS

| | | | |
|---|---|---|---|
| 2,889,848 | 6/1959 | Redmer . | |
| 4,142,524 | 3/1979 | Jassawalla et al. | 128/214 F |
| 4,155,362 | 5/1979 | Jess | 128/214 F |
| 4,199,307 | 4/1980 | Jassawalla | 417/474 |
| 4,236,880 | 12/1980 | Archibald | 417/478 |
| 4,322,201 | 3/1982 | Archibald | 417/279 |
| 4,382,753 | 5/1983 | Archibald | 417/479 |
| 4,397,642 | 8/1983 | Lamadrid | 604/245 |
| 4,586,691 | 5/1986 | Kozlow | 251/7 |
| 4,657,490 | 4/1987 | Abbott | 417/478 |
| 4,689,043 | 8/1987 | Bisha | 604/250 |
| 4,758,220 | 7/1988 | Sundblom et al. | 604/65 |
| 4,878,896 | 11/1989 | Garrison et al. | 604/65 |
| 4,898,579 | 2/1990 | Groshong et al. | 604/67 |
| 4,927,411 | 5/1990 | Pastrone et al. | 604/65 |
| 4,944,485 | 7/1990 | Daoud | 251/9 |
| 5,219,327 | 6/1993 | Okada | 604/250 |
| 5,302,093 | 4/1994 | Owens et al. | 604/153 |

FOREIGN PATENT DOCUMENTS 0450736  10/1991  European Pat. Off. ............ 604/153

*Primary Examiner*—C. Fred Rosenbaum
*Assistant Examiner*—Frank Wilkens, III
*Attorney, Agent, or Firm*—John W. Montgomery; Ross, Clapp, Korn & Montgomery

[57] ABSTRACT

A flow limiter mechanism for use with an infusion pump of the type operating upon a disposable cassette held by the infusion pump and having a flow tube connected to the cassette. The flow limiter includes a receiving channel located on the infusion pump adjacent to the disposable cassette held by the infusion pump. A tube pincher is operatively associated with the receiving channel to pinch the flow tube in a clamped position and mechanically retractable to an unclamped position to allow the flow tube to open. Electrical controls are connected for selectably operating the tube pincher from the clamped closed position to the unclamped opened position while the disposable cassette is held by the infusion pump. A flow clip is attached to the flow tube and is manually operable between opened and closed clipping positions prior to inserting the disposable cassette into the infusion pump. The flow tube and attached flow clip are prevented from being removed from the flow limiter mechanism unless the flow clip is in the closed clipping position.

14 Claims, 5 Drawing Sheets

TUBE FLOW LIMITER, SAFETY FLOW CLIP, AND TUBE PINCHER MECHANISM

CROSS-REFERENCE TO RELATED APPLICATIONS

This is a continuation-in-part filed under 37 C.F.R. §1.53 of prior U.S. patent application Ser. No. 07/880,642, filed May 6, 1992 now abandoned in the United States Patent and Trademark Office.

TECHNICAL FIELD OF THE INVENTION

This invention relates to a flow limiter mechanism for an infusion pump and disposable cassette system, and in particular to a flow limiter mechanism which includes a clip for preventing fluid flow before the cassette is loaded into the pump and after the cassette is unloaded from the infusion pump and also includes a tube pincher associated with the infusion pump for selectively permitting or preventing fluid flow to a patient when the cassette is held in the infusion pump.

BACKGROUND OF THE INVENTION

Infusion of fluids, such as drugs and plasma, into a patient is commonplace in the medical field. Two common infusion methods are intravenous delivery of fluids by gravity and either intravenous or interarterial delivery by mechanically pressurizing the fluids for delivery to the patient. Infusion pumps with disposable cassettes have been employed with the significant advantage of providing a simple disposable element in combination with a relatively straightforward pumping action.

One infusion pump, which incorporates a cassette formed by bonding of two substantially flat sheets, has been disclosed in U.S. Pat. No. 4,657,490. With the use of such disposable cassettes the fluid to be infused into the patient comes into contact only with the cassette. The pumping mechanism itself does not contact the fluid. Thus, the cassettes and associated input and output tubing can be maintained in a sterile condition. The cassette and the tubing are disposed of and replaced between patients or between changes in the fluid to be infused. The new cassettes are loaded into an infusion pump having a cassette receiving section in which the cassette is operated upon by valve members and pumping members of the infusion pump. A pressure sensor monitors the pressure exerted on the cassette and an outlet restriction valve is controlled to maintain accuracy of delivery. The pumping stroke is timed to obtain the desired flow rate. Pressure limits can be set beyond which pumping action will not be performed.

Prior to the present invention, disposable cassette pumping systems have relied upon relatively inconvenient tubing clamps to prevent unwanted flow through the cassette to the patient before the cassette was loaded, while the cassette was being loaded and after it was removed from the cassette receiving section of the pumping mechanism. Care and attention to the external tubing clamps had to be exercised to insure that the flow was completely terminated to avoid rapid or unmetered flow to the patient. When the cassette was loaded, the external clamps were released and the valves for restricting the flow through the cassette were primarily relied upon to accomplish a selected no-flow period of operation while the cassette remained in the pumping device.

Various slide clamps which constrict or obstruct "V" lines are known, including a safety slide clamp as disclosed in Kozlo, U.S. Pat. No. 4,586,691, which comprises a blade formed with a teardrop shaped aperture through which the tubing is positioned having an enlarged portion and a narrow portion. The enlarged portion allows flow through the tubing and tapers to the narrow portion which is engageable with the tubing to prevent flow therethrough. There is a retainer for supporting the blade and retaining the tubing so that the blade can be moved with respect to the tubing to and from the open and closed positions. The clamping blade can be removed from the retainer base only upon first placing the tube into the clamped position and may be received in the base only when the blade is in the clamped position.

Another tube clamp is disclosed in U.S. Pat. No. 4,689,043 for use in a peristaltic infusion pump. It includes a slide clamp which constricts or obstructs the I.V. line similar to that as in Kozlo, however, the clamp is in that the clamp cannot be mounted into the infusion medical device unless the clamp is in the closed position. The device disclosed further cooperates with a handle which urges the clamp from a closed position to an open position when the tube is engaged in the peristaltic pumping mechanism. The handle also automatically operates to urge the clamp from the open position to the closed position prior to and in preparation of the removal of the tube from the peristaltic pumping mechanism.

Other devices are formed, such as stop cock valves, directly in the fluid path within a cast structure interposed in the fluid path. The blade clamps are improvements over such in fluid path valve structures, however currently, such flow clip blade structures either operate automatically so that the flow is automatically opened upon installation of the I.V. tube into the pumping mechanism, or must be in a closed position before installation of the clamp and flow tube into engagement with an infusion pump.

Thus, none of the foregoing art possesses in combination the advantages of the present invention in providing a reliable mechanism with the capability of completely and conveniently stopping the flow of fluid through a disposable cassette, either in or out of the pumping mechanism, such that the cassette cannot be installed unless the flow limiter is in place, such that the flow is automatically closed if the cassette is not held in an operable pumping position, such that the closing or opening of flow through the flow limiter is selectably controlled by the instrument programming when installed, such that the cassette cannot be removed until the flow is closed, such that a clip on the removed cassette can be manually moved from closed to open flow and such that a cassette is installable into the pump whether it is manually clipped closed or opened.

SUMMARY OF THE INVENTION

In accordance with one embodiment of the invention, a reliable flow limiter mechanism is provided for completely stopping flow through a disposable cassette and is sealed to inlet and outlet tubing. The flow limiter mechanism is operatively associated with an infusion pump and includes a tube pincher which automatically pinches the outlet tubing closed if a door holding the cassette in place is opened at any time. The tube pincher can be electrically opened and closed under software control of the fluid pumping mechanism. The flow limiter mechanism also includes a flow clip which is held on the outlet tubing with a carrier and is operable for manually closing the flow through the cassette while it is outside of the pumping mechanism of the infusion pump. The flow clip and carrier are designed for convenient installation onto the cassette. The flow clip and carrier are also conveniently insertable into cooperation with other portions of the flow limiter mechanism both when the flow clip is in a closed clip position and when it is in an open clip position. The flow clip and carrier cooperate as part of the flow limiter mechanism to prevent removal of the disposable cassette unless the flow clip is manually actuated into a closed clip position, thus preventing flow through the cassette.

In accordance with another aspect of the present invention, an infusion pump is provided for pumping fluid to a patient for infusion. The pump includes a pumping mechanism, and a disposable cassette which is sealingly connected to inlet tubing and outlet tubing. The cassette is held in place adjacent the appropriate pumping mechanism by means of a closable door which latches in place. A flow limiter mechanism is mounted to the pump adjacent the pumping mechanism into which the cassette is received. The flow limiter mechanism includes a tube pincher comprising a channel into which the outlet tubing is held by the closable door. Interposed in the channel is a tube pincher arm which blocks insertion of the tubing while the tube pincher is in a closed position. The tube pincher arm is manually movable out of the channel by the operator for insertion of the cassette and outlet tube portion thereinto. Upon insertion of the cassette, the tube pincher arm is manually released to close upon the outlet tube with sufficient compression force to stop the flow of fluid completely. Upon closing the door into a latched position, the tube pincher arm is operable by electrical actuation selectively between an open and a closed position according to control circuitry associated with the pumping mechanism. The flow limiter mechanism further includes a flow clip which is attached and positioned on the outlet tubing of the cassette to be manually actuated by the operator outside of the pumping instrument selectively between an open and a closed position. The flow limiter mechanism further includes a receptacle for the flow clip, which, receptacle will receive the flow clip thereinto, whether it is in an open or a closed position, but which receptacle is designed in operative association with the flow clip to prevent removal of the tube carrier and attached cassette unless the flow clip is in a closed position. Manually moving the flow clip to a closed position actuates the receptacle to allow removal.

In accordance with yet another aspect of the present invention, the flow limiter mechanism includes a tube pincher mechanism which is mechanically biased as with a spring into a closed position. A portion of the tube pincher blocks insertion of the cassette when in a closed position. The bias can be overcome either through a manually pivotable lever arm or through a second pivotable lever arm actuated by an electrical solenoid. The electrical solenoid lever arm becomes mechanically latched in its open position after actuation; however, upon opening of the door, the latching mechanism is released so that the lever arm returns to its biased closed position. A directionally shaped carrier plate holds a flow clip oriented on a portion of tubing sealed to a cassette. A corresponding directionally shaped indentation is formed as a portion of a flow clip receptacle in the flow limiter for receiving the carrier adjacent to the pumping mechanism of an infusion pump. The carrier plate securely holds the tubing and slidably holds the flow clip for manual movement with respect to the tubing perpendicular to the direction of the tubing. The flow clip defines an orifice therethrough sized for non-restrictive passage of the tubing. The flow clip further defines a narrow slit extending from the orifice and having opposed inwardly facing surfaces sufficiently closely spaced such that the tubing can be forced therebetween, to thereby close off the tubing. Thus, when the clip is slid into a first position, the tubing is aligned with the orifice so that the tubing is open, and when the clip is slid to a second position, the tubing becomes lodged between the inwardly facing surfaces of the slit so that the tubing is closed. An automatic gripping means is operatively associated with the carrier, the flow clip, and the flow clip receptacle so that it releases the carrier only when the flow clip is in the closed position with the tubing crimped therebetween. Thus, after the flow clip and carrier are received in the receptacle and directional indentation of the flow limiter mechanism, it can only be removed when the flow clip is manually closed.

BRIEF DESCRIPTION OF THE DRAWINGS

A more complete understanding of the invention may be had by reference to the following detailed description and claims, when taken in conjunction with the accompanying drawings, in which like numerals represent like elements, and wherein:

DETAILED DESCRIPTION OF THE DRAWINGS

Figure 1:
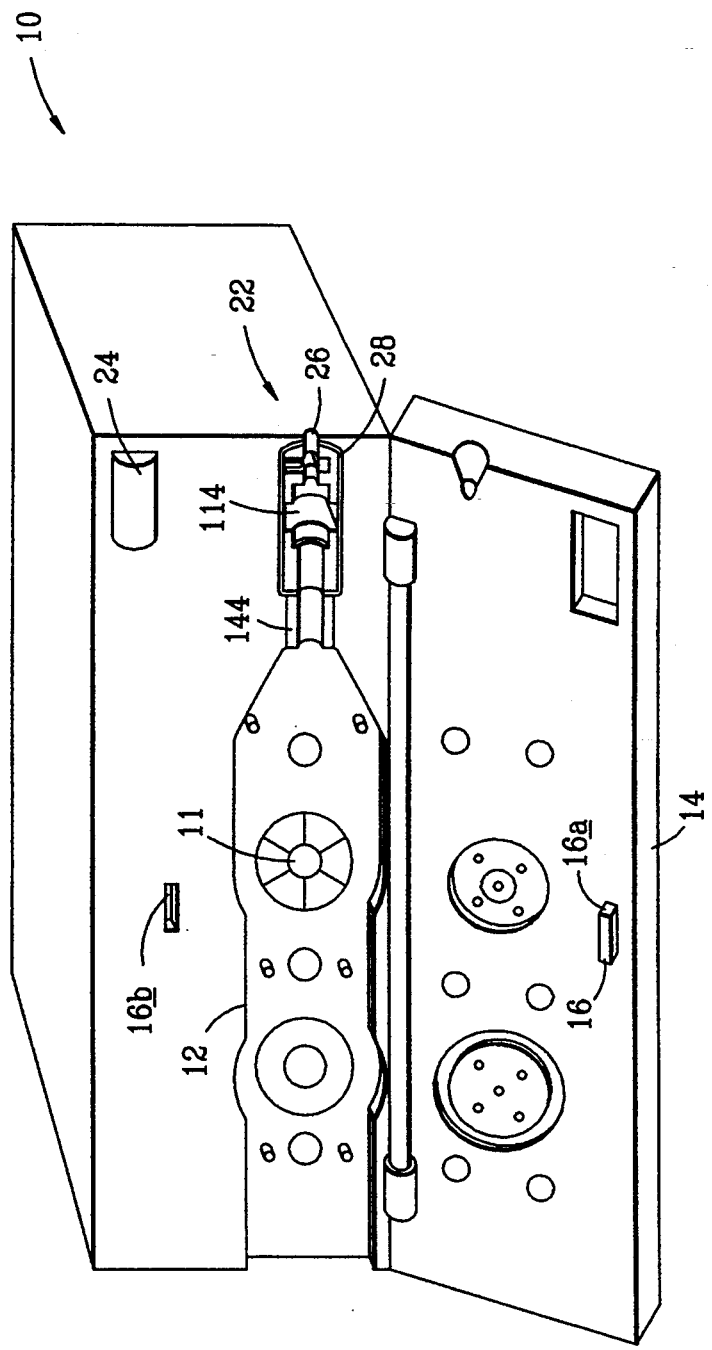
FIG. 1 is a schematic representation of an infusion pump with the flow limiter mechanism mounted adjacent to the pumping mechanism and cassette receiving portion of the infusion pump.

In FIG. 1, infusion pump 10 is shown schematically in a perspective view. The infusion pump 10 has a pumping mechanism 11 in a cassette receiving section 12 and a means for holding the cassette in operable position, such as door 14. Door 14 has a latch 16, which may, for example, comprise a male latch portion 16a and a female portion latch portion 16b, or other suitable latching mechanism, to hold door 14 securely in place for operation of the infusion pump. An exposed portion of a flow limiter assembly 20 is shown in a position adjacent the cassette receiving section 12, in the outlet flow direction. Flow limiter assembly 20 includes a tube pincher 22 and a loading button 24 which cooperates with the internal mechanism of the fluid flow limiter assembly as will be more fully understood with reference to FIGS. 3 and 4 below. There is an outlet tube receiving channel 26 adjacent the pumping mechanism of the infusion pump.

Figure 2:
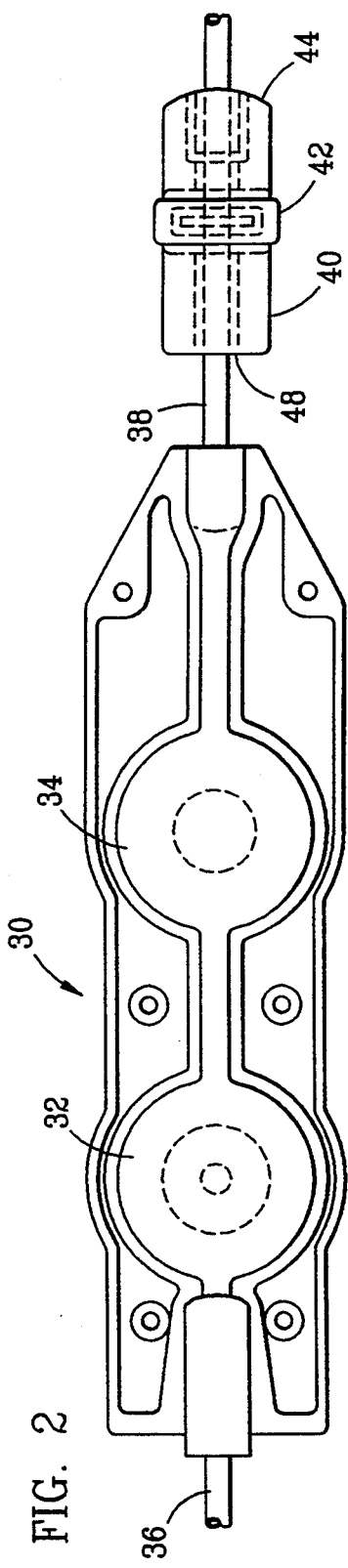
FIG. 2 is a schematic plan view of a disposable cassette having a flow tube attached and upon which the flow limiter of the present invention acts.

A disposable-cassette 30 is shown in a schematic plan view in FIG. 2. It includes a refill reservoir 32, a delivery pumping chamber 34, and sealingly attached inlet tubing 36 and outlet tubing 38. A flow clip carrier 40 carries a flow clip 42 which is slidingly received and held by the flow clip carrier 40. The flow clip carrier 40 has a shape 44 for alignment with a corresponding receptacle 28 which has a correspondingly shaped indentation 46 for alignment of the flow clip carrier therein. The flow clip carrier 40 is positioned along a flow tube, such as outlet tube 38 with a positioning attachment 48. Positioning attachment 48 may, for example, be constructed for plastic welding or adhesion to the output tubing 38.

Figure 3:
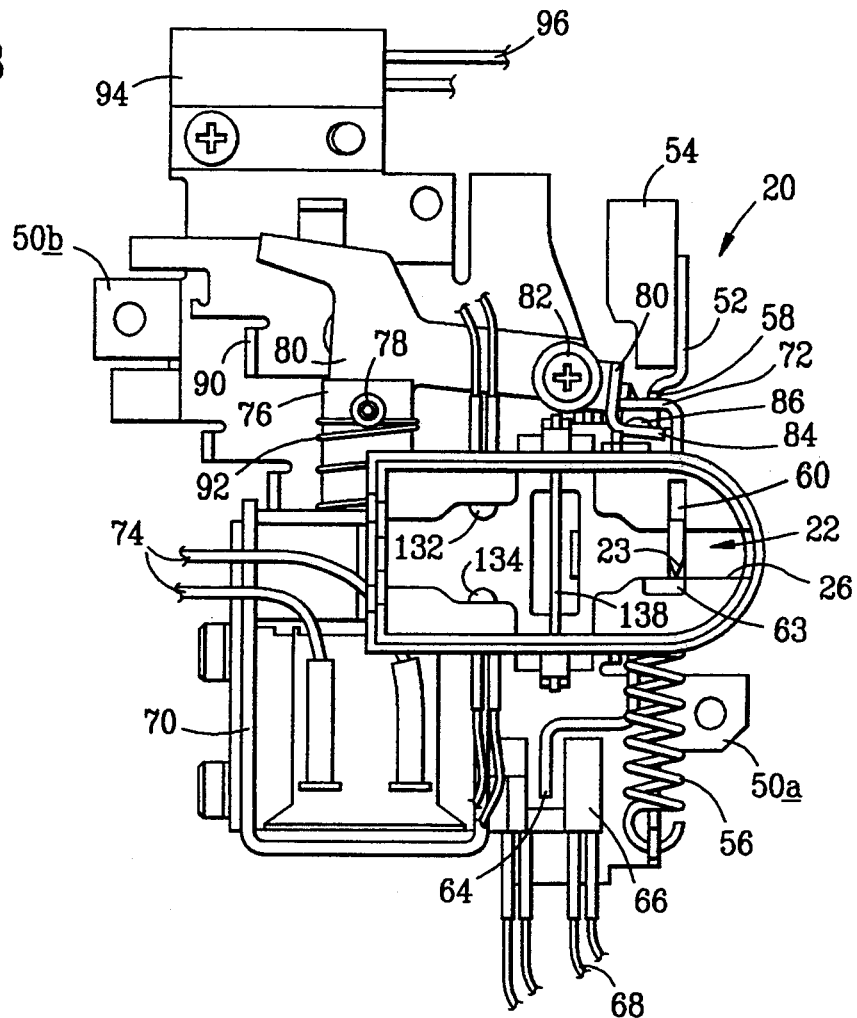
FIG. 3 is an assembled plan view of the flow limiter mechanism according to the present invention.
Figure 4:
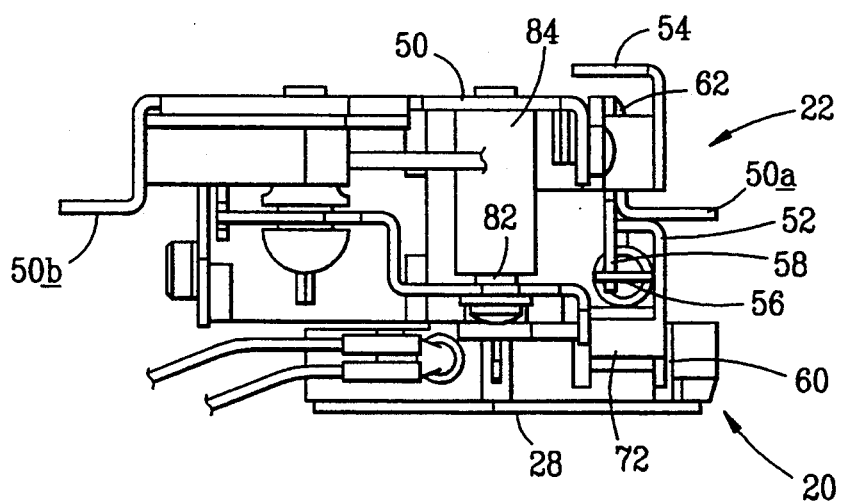
FIG. 4 is a top plan view of the flow limiter and tube pincher mechanism according to the present invention.

With reference to FIG. 3 which is a front plan view and to FIG. 4 which is a top plan view of the fluid flow limiter assembly 20, the construction may be more fully understood. A tube pincher 22 includes a tube pincher lever 52 which is attached to a mechanical actuator 54. The mechanical actuator 54 interacts with and is contacted by loading button 24 (shown in FIG. 1). A spring bias 56 is attached to a pincher lever spring arm 58 for holding the tube pincher lever 52 downwardly into a slot 60 formed partially into channel 26. A support anvil 63 is formed along channel 26 adjacent the slot 60 to support a flow tubing against pinching pressure exerted by lever 52. A portion 23 of the tube pincher lever 52 is interposed into the flow tube channel 26 and the tube pincher lever 52 is mounted about a pivot mount 62, such that the bias spring 56 pivots the pincher portion 23 of tube lever 52 into a downward or closed position. Upon manual actuation of the loading button 24, the mechanical actuator 54, which cooperates with the loading button 24, is actuated, thereby pivoting tube pincher lever 52 and portion 23 thereof upward out of the outlet tube channel 26. This allows the cassette 30 to be inserted into the receiving section 12 and the carrier 40 to be received within receptacle 28. Upon releasing button 24, lever arm 52 is pivoted through the bias action of spring 56 into a downward or pinched closed position. Spring 56 acts through pincher lever spring arm 58 with sufficient force to clamp the outlet tubing completely closed, and to eliminate flow therethrough, even with internal fluid pressures equivalent to 750 mmHg, or greater. Preferably, the mechanical advantage of the lever 52, actuator 54, and button 24 overcomes the bias of spring 56 with a conveniently applied force, preferably about five pounds force, or less.

Attached to lever arm 52 is a position tab 64, which interacts with a position detector 66 so that the position of the lever arm can be electrically monitored through electrical position sensor signal wires 68.

Rigidly attached to pincher lever 52 is a lifting plate 72 for purposes of actuating the lever arm 52 or the tube pincher 22 through electrical control. The electrical control may be provided with a solenoid 70 which is activated to first and second positions with control wires 74. The solenoid piston 76 acts through attachment pin 78 upon lifting lever 80 which is pivotably held mounted at 82 and appropriately spaced from the base plate 50 with mounting cylinder 84. A contact pad 86 is formed at the opposite end of lifting lever 80 from attachment pin 78. Contact pad 86 contacts the lifting plate 72 upon retraction of solenoid piston 76. Contact pad 86 may have a rounded bearing cap 88 to permit reduced friction contact with the underside of lifting plate 72. Thus, when solenoid piston 76 is in its extended position as shown, the lever arm 52 is biased with spring 56 to a downward or clamped closed position. Upon actuation of solenoid 70, piston 76 retracts and pivots about pivot mount 82 so that the contact pad 86, acting through rounded cap 88, lifts against lifting plate 72 thereby raising the clamping arm portions 23 away from anvil 63 and out of the tube channel 26. A position latch mechanism 90 holds the lever arm in its upward position against the bias of spring 56 and also against the bias of solenoid spring 92, even when electrical power through wire 74 is discontinued.

For safety purposes, position latch mechanism 90 is constructed and interconnected with the door latch 16 so that if the door is opened to the infusion pump, latch 90 mechanically forces the release of lifting arm 80 and pincher portion 23 again pinches the outlet tube to prevent further fluid flow, as such flow would then no longer be controlled by the pumping action of the infusion pump. A door sensor 94 is also provided and is interconnected through control wires 96 through a control circuit to control wires 74 of the solenoid so that upon opening of the door 14, as by unlatching latch mechanism 16, the solenoid 72 is electrically released.

Figure 5:
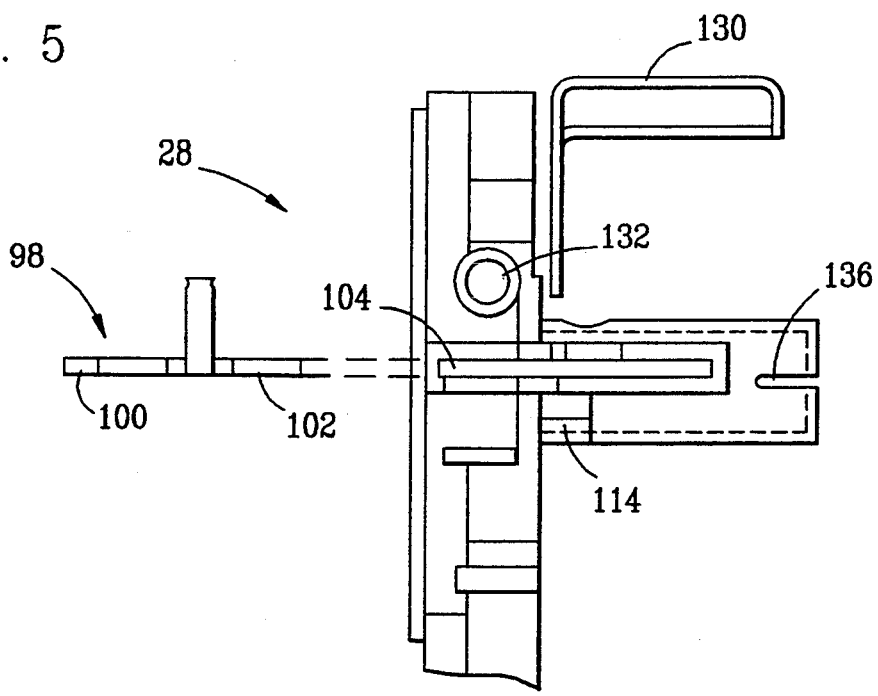
FIG. 5 is a top plan view of the flow limiter tube clip receptacle and gripping mechanism according to the present invention.
Figure 6:
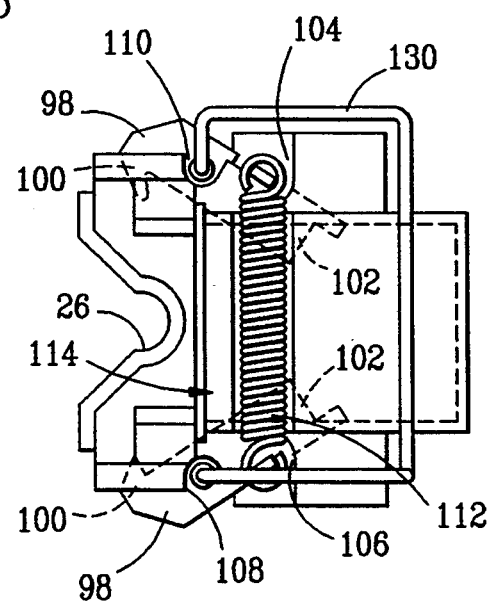
FIG. 6 is a front plan view of the flow limiter tube clip receptacle and gripping mechanism according to the present invention.

The construction and operation of the flow clip, the carrier receptacle 28 and a clip gripping mechanism 96 can be further understood with reference to FIGS. 5 and 6, in which FIG. 5 is a top partially exploded plan view of receptacle 28. FIG. 6 is an end view of receptacle 28. A pair of gripping arms 98 having gripping hooks 100 and tail portions 102 which gripping arms are pivotably held at 108 and 110 within opposed slots 104 and 106 so that they pivot. The gripping arms 98 are biased as with a spring bias means 112 such that the gripping hooks 100 are exterior to a flow clip receiving chamber 114, which receiving chamber 114 is positioned and sized to allow perpendicular sliding motion of a flow clip 42 thereinto. When flow clip 42 is inserted completely into the chamber 114, flow clip sides 124 contact tail portions 102 of gripping arms 98 so that the gripping hooks 100 are moved inwardly against the flow clip carrier 40 and engage detent portions 116 formed on opposed sides of the carrier 40 adjacent the slidable flow clip 42.

Figure 7:
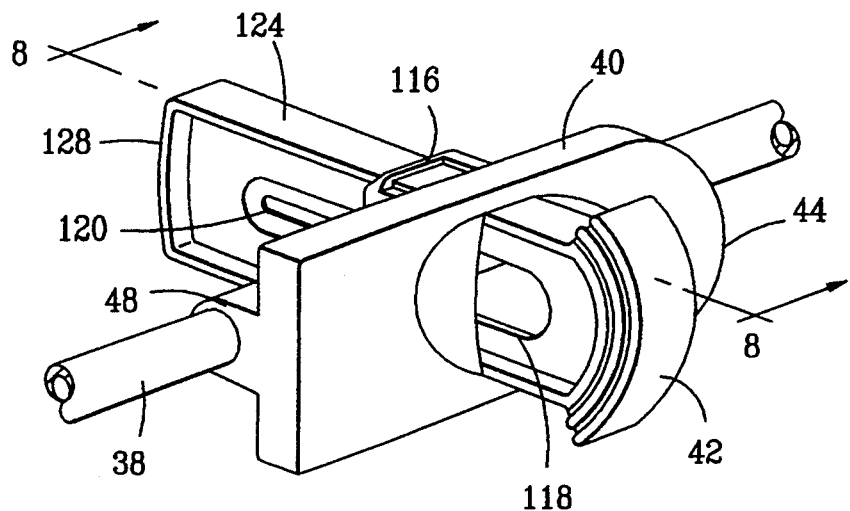
FIG. 7 is a perspective view of the flow tube clip and carrier plate mounted on the flow tubing.
Figure 8:
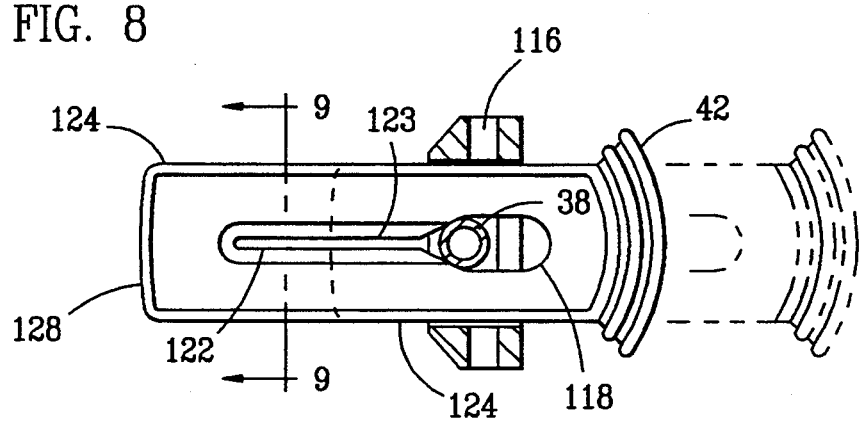
FIG. 8 is a cross-sectional view of the flow clip and carrier of FIG. 7 taken line 8—8.
Figure 9:
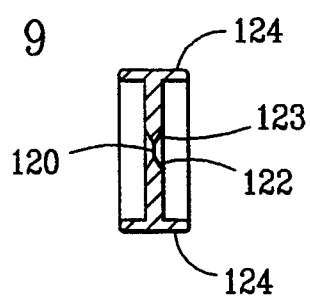
FIG. 9 is a cross-sectional view of the flow clip and carrier of FIG. 8 taken along line 9—9.

FIG. 7 is a perspective view of the flow clip and carrier attached to a portion of an outlet tubing 38, which carrier, clip, and tubing is received and aligned within receptacle 28. FIGS. 8 and 9 are cross-sectional views of the flow clip. There is an orifice 118 through clip 42, which orifice 118 is sized and aligned for passage of tube 38 therethrough perpendicular to the sliding direction of clip 42. The flow clip 42 further defines a narrow slit 120 extending from orifice 118, which narrow slit 120 has opposed inwardly facing surfaces 122 and 124 which are sufficiently closely spaced such that the outlet tubing can be forced therebetween to thereby close off the tubing. Preferably, only a convenient amount of relative force between the tube and clip 42, such as a force of less than about five pounds, is required to slide a tube into the slit. Upon sliding the clip 42 toward the orifice 118, compression force on the tubing is released and it is in an open flow position.

Sliding the clip 42 into channel 114 results in tubing 38 engaging tube channel 26 so that the clip is moved with respect to the tube to the orifice open position. The side walls 124 of clip 42 engage tail portions 102 of the gripping arms 98 and push the gripping hooks 100 into gripping detents 116. The contact between the sides 124 of the clip 42 and the tail portions 102 of the gripping arms 98 keep the hooks 100 engaged while clip 42 is in its open flow position. In this position as described above, the tube pincher mechanism 22 is then activated as described with respect to FIGS. 3 and 4 until such time as cassette 30 is replaced.

To remove cassette 30, it is necessary to release the gripping hooks 100 from detents 116. This is accomplished by pulling the flow clip 42 outward with respect to carrier 40. Carrier 40 is automatically held in place with hooks 100 until the end 128 of clip 42 moves beyond the tail portions 102 of gripping arms 98. Arms 98 pivot automatically, due to bias spring 104, so that hooks 100 retract from detents 116 and carrier 40 is released. Sliding clip 42 relative to tubing 38 in this manner will force the tubing 38 into slit 120, clipping it closed between surfaces 122 and 123. Thus, before removing the cassette 30, the flow clip 42 must be placed into a closed flow position. Also, the tube pincher 22 will be in a closed position due to the opening of door 14. Button 24 can then be manually depressed to lift pincher arm 52 away from tube 38 to complete removal of cassette 30.

Carrier 40 may be inserted into receptacle 20 whether the flow clip is in a closed or open position; if in a closed position, the engagement of hooks 100 will take place upon pushing flow clip 42 completely into slide chamber 114. Arms 98 will automatically be pushed into detents 116. If, however, flow clip 42 is in the open position upon insertion, pivot mechanism 130 has sufficient resiliency to allow hooking arms 98 to move outwardly until hooks 100 drop into detents 116, thereby effecting carrier latching once again.

With reference again to FIG. 3, tubing engagement sensors 132 and 134 are provided. Sensors 132 and 134 may be a light source and a light receptor photocell, respectively, to detect the presence of a tubing 38 within tubing channel 26. Blockage of direct light indicates engagement of a tube 38 and carrier 40 within receptacle 28.

Removal of flow clip 40 from receptacle 28 is assisted by a spring 138 in a channel 136, as shown in FIG. 5, formed at the back of chamber 114. Spring arm 138 biases the flow clip slightly in an outward direction to facilitate ease of removal and to further facilitate firm engagement against hooks 100.

Figure 10:
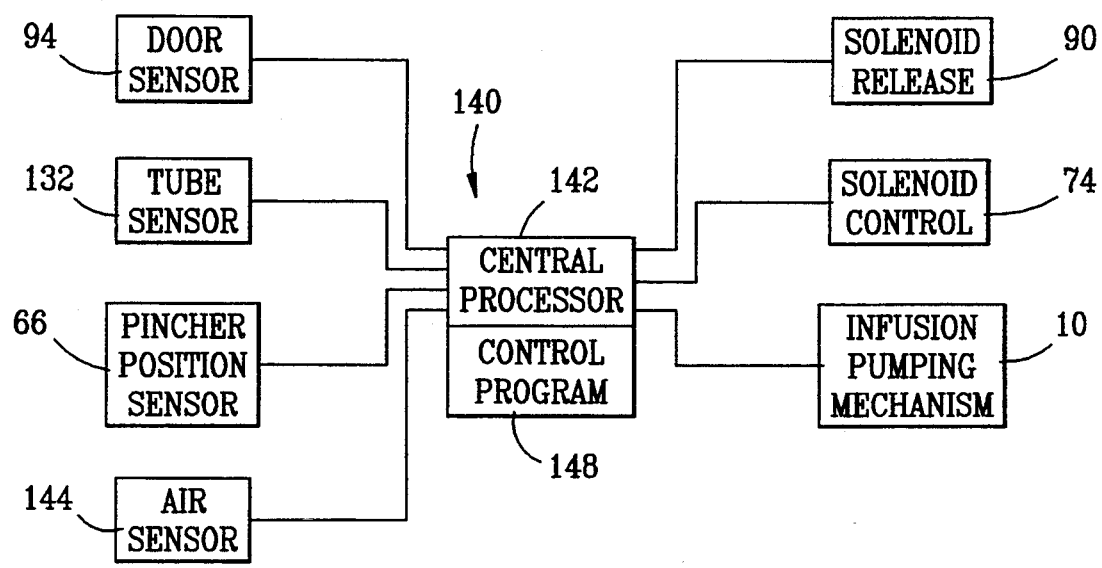
FIG. 10 is a schematic block diagram of a control circuit for the flow limiter according to the present invention.

A schematic diagram of a control circuit 140 is depicted in FIG. 10. In the control circuit 140, there is a door sensor 94 which provides a signal to central processor 142. Sensor 132 also provides a signal to the central processor to indicate insertion of carrier 40. Pincher position sensor 66 signals a closed or open tube pincher position. If desired, an air sensor 144 may be provided to detect air bubbles or voids in the flow tube 38. Each of these sensors detect essentially either a "yes" or a "no" condition. Door sensor 94 signals whether the door 14 is opened or whether it is closed. Flow carrier sensor 132 signals whether the carrier is properly loaded or whether it is not. Position sensor 66 signals whether the tube pincher is in a closed or an open position. Air sensor 144 signals whether there is air in the fluid flow or no air. These signals are provided to the central processor 142 which acts upon the provided information according to a program 148 which, for example, may be contained in software, on a computer chip, may be entered by an operator through a keyboard, or the like. The signal from door sensor 94 is preferably acted upon by the central processor 142 according to a program to electrically enable the solenoid 70 for energization by control wires 74 and also to enable the infusion pumping mechanism. The signal from carrier sensor 132 is also used to enable the infusion pumping mechanism such that if either the door 14 is unlatched or the carrier 40 is not properly loaded into the flow carrier receptacle 28, then pumping action will not be initiated and/or an appropriate alarm signal will be given to the operator so that corrective action can be taken. Once the carrier 40 is properly loaded and the door is properly closed, then the signal from pincher position sensor 66 is received by the central processor 142 to energize the solenoid 70 from a closed to an open position or from an open to a closed position according to the program 148. The pincher position sensor 66 confirms that the desired action takes place and if confirmation is not received, an appropriate alarm signal may be activated. Further, if the pincher position sensor 66 detects that the pincher is in a closed position, then the pump mechanism may be disabled to avoid overpressurizing the cassette and overworking the pump mechanism due to inordinately high pressures caused by the closed tube pincher.

The air sensor 144 can also be used to provide the central processor 142 with information, and if air is sensed for a significant period of time, then the central processor can respond by disabling the pump and by activating the solenoid control to close the tube pincher, to allow the pincher arm 23 to close. Further, an appropriate alarm may be energized to notify the operator of the occlusion condition so that corrective measures may be taken.

Thus, what has been disclosed is a tube flow limiter mechanism having a tube pincher mechanism and a safety flow clip which cooperate to provide a mechanism which reduces the possibility for unchecked free fluid flow and which is conveniently operable and substantially manually actuated to secure non-flow condition unless manually actuated to open the flow or actuated through electrical control to allow flow therethrough.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A flow limiter mechanism in an infusion pump of the type having a channel for receiving a flow tube connected to a disable pumping cassette, said flow limiter mechanism comprising:

a) a tube pincher operatively associated with said receiving channel, said tube pincher having a clamped position to stop flow in said flow tube received in said receiving channel, and said tube pincher having an unclamped position to allow flow in said flow tube, and which tube pincher is mechanically retractable to an unclamped position;

b) electrical controls for selectably operating said tube pincher from said clamped position to said unclamped position while said flow tube connected to said disposable cassette is received in said receiving channel of said infusion pump;

c) a flow clip attached to said flow tube manually operable between opened and closed clipping positions prior to receiving said flow tube into said receiving channel; and d) means cooperatively associated between said flow clip and said receiving channel for preventing removal of said flow tube from said receiving channel when said flow clip is in said opened position and for permitting removal of said flow tube from said receiving channel when said flow clip is in said closed clipping position.

2. A flow limiter mechanism as in claim 1 wherein said tube pincher further comprises:

a) a slot perpendicular to and partially through said receiving channel;

b) a pincher lever arm pivotally mounted to said flow limiter mechanism aligned with said perpendicular slot and positioned for selectable pivoting into and out of said receiving channel;

c) an anvil surface positioned adjacent said perpendicular slot for supporting said flow tube in said receiving channel against said pincher lever arm so that it is compressed therebetween when said pincher lever arm pivots through said perpendicular slot into said receiving channel against said flow tube received in said receiving channel;

d) a spring, biased for pivoting said pincher lever arm at least partially through said perpendicular slot into said receiving channel so that receiving said flow tube into said receiving channel is blocked thereby; and e) a manual actuation device connected to said pincher lever arm for mechanically pivoting the arm against said spring bias out of said receiving channel to allow receiving said flow tube thereinto.

3. A flow limiter mechanism as in claim 2 wherein the electrical controls for selectably operating said tube pincher from said clamped position to said unclamped position further comprises:

a) a lifting lever pivotably mounted to said flow limiter mechanism and having an end for contacting said pincher lever arm; and b) a solenoid connected to said lifting lever arm for pivoting said end thereof to contact said pincher lever arm and to thereby lift said pincher lever arm to said open position.

4. A flow limiter mechanism as in claim 1 wherein said means cooperatively associated with said flow clip and said receiving channel for preventing removal of said flow tube from said receiving channel further comprises:

a) a clip carrier attached to said flow tube of said disposable cassette and slidably holding said flow clip perpendicular to said flow tube;

b) a carrier receptacle mounted adjacent said receiving channel for receiving said clip carrier, said flow clip held by said clip carrier and by said flow tube to which said flow clip is attached, all in a predetermined alignment; and c) gripping arms pivotally mounted in said carrier receptacle aligned with said flow clip for gripping said clip carrier upon receiving said clip carrier when said flow clip is in said opened clipping position and for releasing said clip carrier when said flow clip is in said closed clipping position.

5. A flow limiter mechanism as in claim 1 wherein said flow clip which is manually operable between said opened and closed clipping positions, further comprises a clip body defining an orifice sized for passing said flow tube therethrough, and defining a slit interconnected with said orifice, said slit having walls spaced apart a sufficiently wide distance to allow said flow tube to be manually slid into said slit with application of conveniently low force and said walls spaced apart a sufficiently close distance to clip said flow tube closed when said flow tube is slid into said slit.

6. A flow limiter mechanism as in claim 4 further comprising:

a) a central processor interconnected to said electrical controls of said tube pincher;

b) a door operatively associated with said flow limiter mechanism having a first closed position for holding said disposable pumping cassette with said flow tube in said receiving channel and a second open position for releasing said disposable pumping cassette;

c) a door sensor interconnected with said door for providing a signal to said central processor indicating whether said door is in a first closed or a second opened position;

d) a carrier sensor interconnected to provide a signal to said central processor indicating whether said flow clip carrier is properly installed in said receiving channel; and e) a central processor program for enabling said electrical controls of said tube pincher to be activated between said first closed and said second opened position upon receiving signals both from said door sensor indicating that it is in said first closed position and also from said carrier sensor indicating that a clip carrier is properly installed.

7. A flow limiter mechanism as in claim 1 further comprising:

a) a tube pincher lever pivotably mounted to said flow limiter mechanism having an engaged and a disengaged pivot position and having a portion thereof for engaging against said flow tube of said disposable cassette with sufficient force to pinch said flow tube closed in said engaged position and a second portion thereof for mechanically pivoting said tube pincher lever between said engaged and disengaged positions; and b) a loading button mounted on said flow limiter mechanism and operable with a conveniently low manual force for contacting said second portion of said tube pincher lever arm to pivot said engaging portion out of said engaged position.

8. A flow limiter mechanism for limiting flow in a disposable pumping cassette of the type having flow tubing connected to and extending from said pumping cassette, said flow limiter mechanism comprising:

a) a channel into which channel said flow tubing is received;

b) a tube pincher operatively associated with said receiving channel having a first position in which said received flow tubing is mechanically pinched to stop flow therein and having a second position at which said tube pincher is retracted from said received flow tubing to allow flow therein;

c) mechanical means for retracting said tube pincher from said clamped position;

d) electrical controls for selectably operating said tube pincher from said first position to said second position while said flow tubing is received in said receiving channel;

e) a flow clip, attached to said flow tubing, separately from said tube pincher, having an opened clipping position and a closed clipping position, said flow clip manually movable between said opened clipping position and said closed clipping position before said flow tubing is received into said receiving channel; and f) clip receiving means for receiving said flow clip attached to said flow tubing, said clip receiving means cooperatively associated with said flow clip and with said receiving channel for preventing removal of said flow clip and said attached flow tubing therefrom, unless said flow clip is in said closed clipping position.

9. A flow limiter mechanism as in claim 8 wherein said tube pincher further comprises:

a) a slot perpendicular to and partially through said receiving channel;

b) a pincher lever arm pivotally mounted to said flow limiter mechanism aligned with said perpendicular slot and positioned for selectable pivoting into and out of said receiving channel;

c) an anvil surface positioned adjacent said perpendicular slot for supporting said flow tubing in said receiving channel against said pincher lever arm so that it is compressed therebetween when said pincher lever arm pivots through said perpendicular slot into said receiving channel against an inserted flow tube;

d) a bias means for pivoting said pincher lever arm at least partially through said perpendicular slot into said receiving channel so that receiving of said flow tubing into said receiving channel is blocked thereby; and e) wherein said mechanical means for retracting includes a manual actuation device connected to said pincher lever arm for pivoting said lever arm against said bias means out of said receiving channel, thereby allowing said flow tubing to be received thereinto.

10. A flow limiter mechanism as in claim 8 wherein said electrical controls for selectably operating said tube pincher between said clamped and said unclamped positions further comprises:

a) a lifting lever pivotably mounted to said flow limiter mechanism and having an end for contacting said pincher lever arm; and b) an electrical a solenoid connected to said lifting lever arm for pivoting said end of said lifting level to contact said pincher lever arm and to thereby lift said pincher lever arm to said open position.

11. A flow limiter mechanism as in claim 8 wherein said means cooperatively associated with said flow clip and with said receiving channel for preventing removal of said flow tubing from said receiving channel further comprises:

a) a clip carrier attached to said flow tubing of said disposable cassette and slidably holding said flow clip perpendicular to said flow tubing;

b) a carrier receptacle mounted adjacent to said receiving channel for receiving said clip carrier, said flow clip held by said clip carrier, and said flow tubing to which said flow clip is attached, all received in a predetermined alignment; and c) gripping arms pivotally mounted in said carrier receptacle aligned with said flow clip for gripping said clip carrier upon receiving said clip carrier when said flow clip is in its opened clipping position and for releasing said clip carrier when said flow clip is in said closed clipping position.

12. A flow limiter mechanism as in claim 8 wherein said flow clip which is manually operable between said opened and closed clipping positions, further comprises a clip body defining an orifice sized for passing a flow tubing therethrough, and defining a slit interconnected with said orifice, said slit having walls spaced apart a sufficiently wide distance to allow said flow tubing to be manually slid into said slit with application of conveniently low force and said walls spaced apart a sufficiently close distance to clip said flow tube closed when said flow tube is slid into said slit.

13. A flow limiter mechanism as in claim 11 further comprising:

a) a central processor interconnected to said electrical controls of said tube pincher;

b) a door operatively associated with said flow limiter mechanism having a first closed position for holding said cassette with said flow tube in said receiving channel and a second open position for releasing said cassette;

c) a door sensor interconnected with said door for providing a signal to said central processor indicating whether said door is in a first closed or a second opened position;

d) a carrier sensor interconnected to provide a signal to said central processor indicating whether said flow clip carrier is properly installed in said receiving channel; and e) a central processor program for enabling said electrical controls of said tube pincher to be activated between said first closed and said second opened position upon receiving signals both from said door sensor indicating that it is in said first closed position and also from said carrier sensor indicating that a clip carrier is properly installed.

14. A flow limiter mechanism as in claim 1 further comprising:

a) a tube pincher lever pivotably mounted to said infusion pump having an engaged and a disengaged pivot position and having a portion thereof for engaging against a flow tube of a disposable cassette with sufficient force to pinch said flow tube closed in said engaged position and a second portion thereof for mechanically pivoting said tube pincher lever between said engaged and disengaged positions; and b) a loading button mounted on said infusion pump and operable with a conveniently low manual force for contacting said second portion of said tube pincher lever arm to pivot said engaging portion out of said engaged position.

* * * * *